(12) United States Patent
George et al.

(10) Patent No.: US 9,042,634 B2
(45) Date of Patent: May 26, 2015

(54) METHOD SYSTEM AND COMPUTER PRODUCT FOR NON-DESTRUCTIVE OBJECT ANALYSIS

(71) Applicant: General Electric Company, Schenectady, NY (US)

(72) Inventors: Sheri George, Bangalore (IN); Haribaskar Govindasamy, Bangalore (IN); Utkarsh Madhav Kulkarni, Bangalore (IN); Pavel Pokutnev, Wunstorf (DE); Marko Rosenmueller, Wunstorf (DE); Alexander Suppes, Wunstorf (DE)

(73) Assignee: General Electric Company, Schenectady, NY (US)

( * ) Notice: Subject to any disclaimer, the term of this patent is extended or adjusted under 35 U.S.C. 154(b) by 152 days.

(21) Appl. No.: 13/741,957

(22) Filed: Jan. 15, 2013

(65) Prior Publication Data

US 2014/0198946 A1    Jul. 17, 2014

(51) Int. Cl.
| | |
|---|---|
| *G06K 9/00* | (2006.01) |
| *G06T 7/00* | (2006.01) |
| *G06T 3/00* | (2006.01) |
| *G01N 23/04* | (2006.01) |

(Continued)

(52) U.S. Cl.
CPC .......... *G06K 9/3241* (2013.01); *G01N 29/0609* (2013.01); *G01N 29/0645* (2013.01); *G01N 29/069* (2013.01); *G01N 29/11* (2013.01); *G01N 29/226* (2013.01); *G06T 7/0004* (2013.01); *G06T 2207/10081* (2013.01); *G06T 2207/30164* (2013.01)

(58) Field of Classification Search
CPC ... G06T 7/0004; G06T 7/0006; G06T 7/0051; G06T 3/0031; G06T 3/0073; G06T 3/0043; G06T 11/003; G06T 11/20; G06T 11/203; G06T 17/30; G06T 2207/30164; G01N 23/04; G01N 23/046; G01M 15/14
USPC .................................. 382/141, 152, 154, 276
See application file for complete search history.

(56) References Cited

U.S. PATENT DOCUMENTS

| | | | | |
|---|---|---|---|---|
| 5,119,408 | A | * | 6/1992 | Little et al. ........................ 378/4 |
| 5,278,948 | A | * | 1/1994 | Luken, Jr. ..................... 345/423 |

(Continued)

FOREIGN PATENT DOCUMENTS

| | | | |
|---|---|---|---|
| EP | 0905509 | A1 * | 3/1999 |
| EP | 1696388 | A1 * | 8/2006 |
| WO | 0108102 | A1 | 2/2001 |

OTHER PUBLICATIONS

Nolan et al. "X-ray Inspection Utilizing Knowledge Based Feature Isolation with a Neural Network Classifier." SPIE Image Understanding and the Man-Machine Interface. 1472. (1991): 157-164.*

(Continued)

*Primary Examiner* — Michael A Newman
(74) *Attorney, Agent, or Firm* — Hiscock & Barclay LLP (57) ABSTRACT

Aspects of the invention provide a solution for analyzing an object, such as a part of a turbo machine. A planar surface is generated using a curved reformat function based on a surface of a three-dimensional (3D) image of an object. A peel of the 3D image that is adjacent to the surface is determined. Based on the peel, a second planar surface is generated. These two, and/or other similarly generated planar surfaces can be analyzed to determine characteristics of the original object.

20 Claims, 10 Drawing Sheets

(51) Int. Cl.
*G01M 15/14* (2006.01)
*G06K 9/32* (2006.01)
*G01N 29/06* (2006.01)
*G01N 29/11* (2006.01)
*G01N 29/22* (2006.01)

(56) References Cited

U.S. PATENT DOCUMENTS

| | | | | |
|---|---|---|---|---|
| 5,313,567 | A | * | 5/1994 | Civanlar et al. ............... 345/424 |
| 6,204,860 | B1 | | 3/2001 | Singh |
| 6,526,117 | B1 | | 2/2003 | Okerlund et al. |
| 6,968,032 | B2 | | 11/2005 | Mohr et al. |
| 7,211,046 | B2 | | 5/2007 | Deller et |
| 7,236,167 | B2 | * | 6/2007 | Lee et al. ...................... 345/420 |
| 7,545,903 | B2 | | 6/2009 | Kohler et al. |
| 7,924,972 | B2 | | 4/2011 | Koehler et al. |
| 7,940,974 | B2 | | 5/2011 | Skinner et al. |
| 8,359,114 | B2 | * | 1/2013 | Steingart et al. ................ 700/98 |
| 8,370,293 | B2 | | 2/2013 | Iwase et al. |
| 8,730,237 | B2 | * | 5/2014 | Ruijters et al. ................ 345/424 |
| 2004/0249270 | A1 | * | 12/2004 | Kondo et al. ................. 600/425 |
| 2010/0131887 | A1 | * | 5/2010 | Salazar-Ferrer et al. ..... 715/788 |
| 2011/0102430 | A1 | * | 5/2011 | Eberhard et al. ............... 345/420 |
| 2012/0007851 | A1 | * | 1/2012 | Matsumoto ................... 345/419 |
| 2012/0169735 | A1 | * | 7/2012 | Nijlunsing .................... 345/424 |

OTHER PUBLICATIONS

Huang, et al. "Visualizing Industrial CT Volume Data for Nondestructive Testing Applications." Proceedings of the 14th IEEE Visualization Conference. 14. (2003): 547-554.*

Lampe, et al. "Curve-Centric Volume Reformation for Comparative Visualization." IEEE Transactions on Visualization and Computer Graphics. 15.6 (2009): 1235-1242.*

Green, et al. United States. Army Research Laboratory. Nondestructive Evaluation of Damaged and As-Fabricated Encapsulated Ceramic Panels. Aberdeen Proving Ground: , 2009.*

Pham, "Offset Curves and Surfaces: A Brief Survey", Computer Aided Design, Elsevier Publishers BV:, vol. No. 24, Issue No. 4, pp. 223-229, Apr. 1, 1992.

Nolan et al., "X-Ray Inspection Utilizing Knowledge Based Feature Isolation With a Neural Network Classifier", Proc. SPIE 1472, Image Understanding and the Man-Machine Interface III, pp. 157-164, Aug. 1, 1991.

PCT Search Report and Written Opinion issued in connection with corresponding Application No. PCT/US2014/010512 on Apr. 8, 2014.

* cited by examiner

METHOD SYSTEM AND COMPUTER PRODUCT FOR NON-DESTRUCTIVE OBJECT ANALYSIS

BACKGROUND OF THE INVENTION

The subject matter disclosed herein relates generally to defect detection. More specifically, the present invention relates to detection of irregularities in a part of a mechanical machine, such as turbo machine part.

In a modern mechanical machine, such as a turbo machine, a plurality of parts work together to perform the machine's function. These parts must be assembled in such a way that all of the parts mesh together correctly. This often requires exact tolerances for such parts elements as part size and/or dimensions and/or the size and/or dimensions of any hole, slot, etc., that is located in the part. A variance in any of these tolerances can cause the part and/or the machine as a whole not to function for its intended purpose. Additionally, or in the alternative, a variance in any of these tolerances can cause a decrease in the lifespan of a machine part. In a high-stress environment, this can lead to an abrupt failure in such a part.

One example of a potentially high-stress environment is a turbo machine. Conventional turbo machines (e.g., gas turbine, steam turbine) are frequently utilized to generate power. More specifically, a working fluid such as hot gas or steam is conventionally forced across sets of turbo machine blades, which are coupled to the rotor of the turbo machine. The force of the working fluid on the blades causes those blades (and the coupled body of the rotor) to rotate. In many cases, the rotor body is coupled to the drive shaft of a dynamoelectric machine such as an electric generator. In this sense, initiating rotation of the turbo-machine rotor can initiate rotation of the drive shaft in the electric generator, and cause that generator to generate an electrical current (associated with power output).

BRIEF DESCRIPTION OF THE INVENTION

Aspects of the invention provide a solution for analyzing an object, such as a part of a turbo machine. A planar surface is generated using a curved reformat function based on a surface of a three-dimensional (3D) image of an object. A peel of the 3D image that is adjacent to the surface is determined. Based on the peel, a second planar surface is generated. These two, and/or other similarly generated planar surfaces can be analyzed to determine characteristics of the original object.

A first aspect of the invention provides a method for analyzing an object, the method comprising: generating, using a computer device, a planar surface from a curved reformat function based on a surface of a 3D image of an object; determining, using the computer device, a peel of the 3D image, the peel being an adjacent surface of the 3D image that is parallel to the surface; and generating using the computer device, a second planar surface from a curved reformat function based on the peel; and analyzing using the computer device, the planar surface and the second planar surface to determine a characteristic of the object.

A second aspect of the invention provides a system for analyzing an object comprising at least one computer device that performs a method, comprising: generating a planar surface from a curved reformat function based on a surface of a 3D image of an object; determining a peel of the 3D image, the peel being an adjacent surface of the 3D image that is parallel to the surface; generating a second planar surface from a curved reformat function based on the peel; and analyzing the planar surface and the second planar surface to determine a characteristic of the object.

A third aspect of the invention provides a program product stored on a computer readable storage device with instructions encoded thereon for analyzing an object, which, when executed, performs a method, comprising: generating a planar surface from a curved reformat function based on a surface of a 3D image of an object; determining a peel of the 3D image, the peel being an adjacent surface of the 3D image that is parallel to the surface; and generating a second planar surface from a curved reformat function based on a remainder surface of the remainder 3D image; and analyzing the planar surface and the second planar surface to determine a characteristic of the object.

Still yet, any of the parts of the present invention could be deployed, managed, serviced, etc., by a service provider who offers to implement the teachings of this invention in a computer system.

Embodiments of the present invention also provide related systems, methods and/or program products.

BRIEF DESCRIPTION OF THE DRAWING

These and other features of the disclosure will be more readily understood from the following detailed description of the various aspects of the invention taken in conjunction with the accompanying drawing that depict various aspects of the invention, in which.

It is noted that the drawings are not to scale. The drawing is intended to depict only typical aspects of the invention, and therefore should not be considered as limiting the scope of the invention.

DETAILED DESCRIPTION OF THE INVENTION

As indicated above, aspects of the invention provide a solution for analyzing an object, such as a part of a turbo machine. A planar surface is generated using a curved reformat function based on a surface of a three-dimensional (3D) image of an object. A peel of the 3D image that is adjacent to the surface is determined. Based on the peel, a second planar surface is generated. These two, and/or other similarly generated planar surfaces can be analyzed to determine characteristics of the original object.

Figure 1:
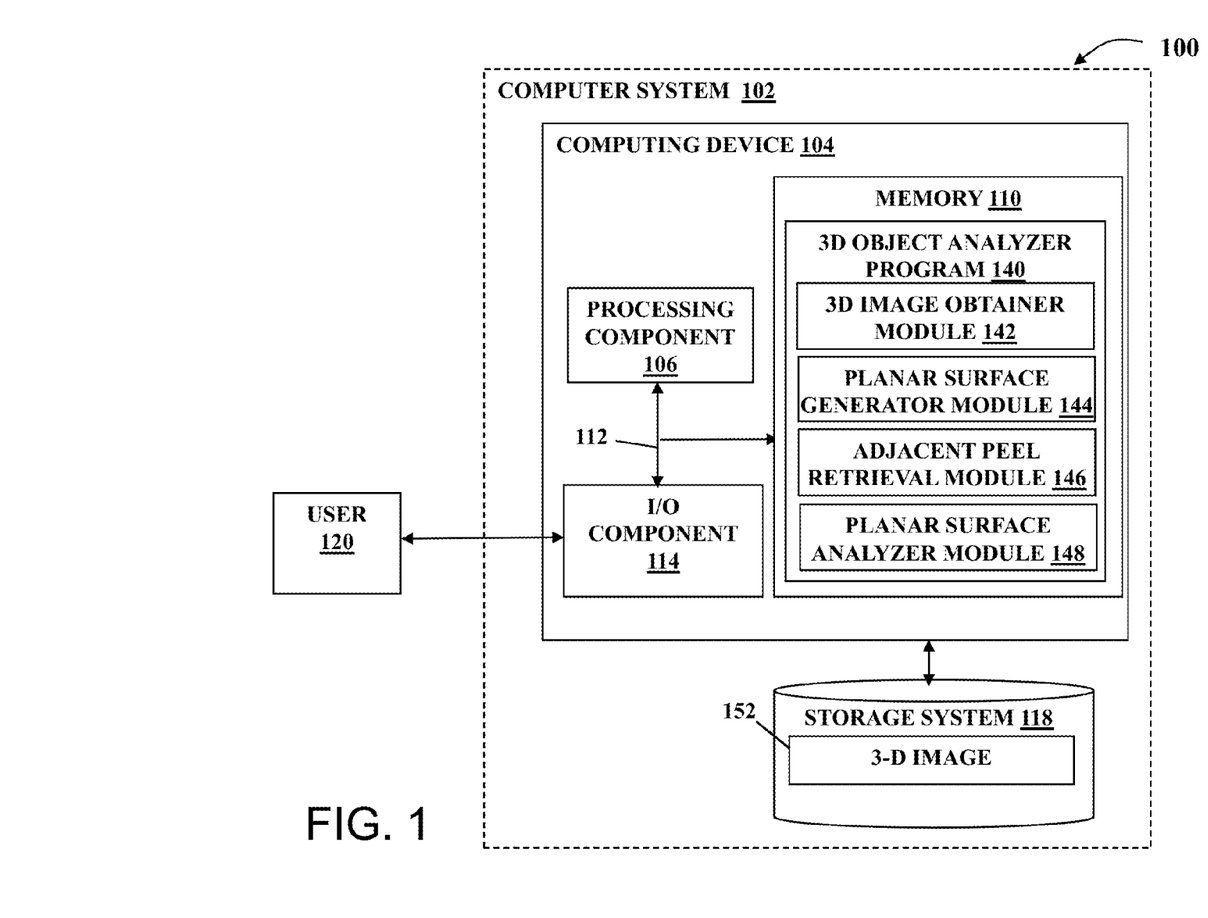
FIG. 1 shows an illustrative computer system according to embodiments of the present invention.

Turning to the drawings, FIG. 1 shows an illustrative environment 100 for analyzing a 3D object. To this extent, environment 100 includes a computer system 102 that can perform a process described herein in order to analyze a 3D object. In particular, computer system 102 is shown including a computing device 104 that includes a 3D object analyzer program 140, which makes computing device 104 operable to analyze a 3D object by performing a process described herein.

Computing device 104 is shown including a processing component 106 (e.g., one or more processors), a memory 110, a storage system 118 (e.g., a storage hierarchy), an input/output (I/O) component 114 (e.g., one or more I/O interfaces and/or devices), and a communications pathway 112. In general, processing component 106 executes program code, such as 3D object analyzer program 140, which is at least partially fixed in memory 110. To this extent, processing component 106 may comprise a single processing unit, or be distributed across one or more processing units in one or more locations.

Memory 110 also can include local memory, employed during actual execution of the program code, bulk storage (storage 118), and/or cache memories (not shown) which provide temporary storage of at least some program code in order to reduce the number of times code must be retrieved from bulk storage 118 during execution. As such, memory 110 may comprise any known type of temporary or permanent data storage media, including magnetic media, optical media, random access memory (RAM), read-only memory (ROM), a data cache, a data object, etc. Moreover, similar to processing component 116, memory 110 may reside at a single physical location, comprising one or more types of data storage, or be distributed across a plurality of physical systems in various forms.

While executing program code, processing component 106 can process data, which can result in reading and/or writing transformed data from/to memory 110 and/or I/O component 114 for further processing. Pathway 112 provides a direct or indirect communications link between each of the components in computer system 102. I/O component 114 can comprise one or more human I/O devices, which enable a human user 120 to interact with computer system 102 and/or one or more communications devices to enable a system user 120 to communicate with computer system 102 using any type of communications link.

To this extent, 3D object analyzer program 140 can manage a set of interfaces (e.g., graphical user interface(s), application program interface, and/or the like) that enable human and/or system users 120 to interact with 3D object analyzer program 140. Users 120 could include quality control personnel who want to insure that appropriate tolerances are met during a manufacture process, among others. Further, 3D object analyzer program 140 can manage (e.g., store, retrieve, create, manipulate, organize, present, etc.) the data in storage system 118, including, but not limited to one or more 3D images 152, using any solution.

In any event, computer system 102 can comprise one or more computing devices 104 (e.g., general purpose computing articles of manufacture) capable of executing program code, such as 3D object analyzer program 140, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, 3D object analyzer program 140 can be embodied as any combination of system software and/or application software. In any event, the technical effect of computer system 102 is to provide processing instructions to computing device 104 in order to analyze a 3D object.

Further, 3D object analyzer program 140 can be implemented using a set of modules 142-148. In this case, a module 142-148 can enable computer system 102 to perform a set of tasks used by 3D object analyzer program 140, and can be separately developed and/or implemented apart from other portions of 3D object analyzer program 140. As used herein, the term "component" means any configuration of hardware, with or without software, which implements the functionality described in conjunction therewith using any solution, while the term "module" means program code that enables a computer system 102 to implement the actions described in conjunction therewith using any solution. When fixed in a memory 110 of a computer system 102 that includes a processing component 106, a module is a substantial portion of a component that implements the actions. Regardless, it is understood that two or more components, modules, and/or systems may share some/all of their respective hardware and/or software. Further, it is understood that some of the functionality discussed herein may not be implemented or additional functionality may be included as part of computer system 102.

When computer system 102 comprises multiple computing devices 104, each computing device 104 may have only a portion of 3D object analyzer program 140 fixed thereon (e.g., one or more modules 142-148). However, it is understood that computer system 102 and 3D object analyzer program 140 are only representative of various possible equivalent computer systems that may perform a process described herein. To this extent, in other embodiments, the functionality provided by computer system 102 and 3D object analyzer program 140 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 102 includes multiple computing devices 104, the computing devices can communicate over any type of communications link. Further, while performing a process described herein, computer system 102 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As discussed herein, 3D object analyzer program 140 enables computer system 102 to analyze a 3D object. To this extent, 3D object analyzer program 140 is shown including a 3D object obtainer module 142, a planar surface generator module 144, a adjacent peel retrieval module 146, and a planar surface analyzer module 148.

3D object obtainer module 142, as executed by computer system 102, obtains a 3D image 152 of an object. The object for which the 3D image 152 is obtained can be any three dimensional object now known or later developed for which analysis is desired. In an embodiment, the object can be an object that is designed to be a part of a complex machine. In an embodiment, the object can be a part of a turbo machine, such as a blade or a nozzle of a turbo machine.

Figure 2:
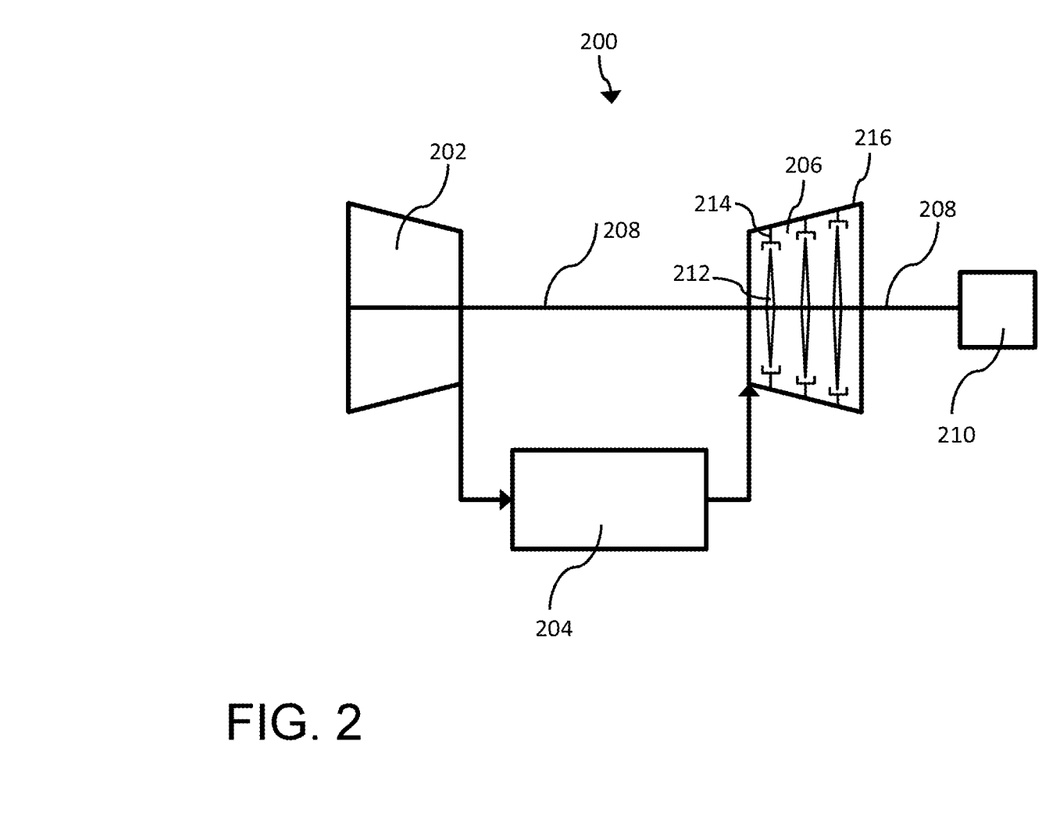
FIG. 2 shows a schematic diagram of an example turbo machine according to embodiments of the present invention.

Turning to FIG. 2, a schematic depiction of a turbo machine is shown according to embodiments of the invention. Turbo machine 200, as shown in FIG. 2 may be a conventional gas turbine system. However, it is understood that turbo machine 200 may be configured as any conventional turbine system (e.g., steam turbine system) configured to generate power. As such, a brief description of the turbo machine 200 is provided for clarity. As shown in FIG. 2, turbo machine 200 may include a compressor 202, combustor 204 fluidly coupled to compressor 202 and a gas turbine component 206 fluidly coupled to combustor 204 for receiving a combustion product from combustor 204. Gas turbine component 206 may also be coupled to compressor 202 via shaft 208. Shaft 208 may also be coupled to a generator 210 for creating electricity during operation of turbo machine 200.

During operation of turbo machine 200, as shown in FIG. 2, compressor 202 may take in air and compress the inlet air before moving the compressed inlet air to the combustor 204. Once in the combustor 204, the compressed air may be mixed with a combustion product (e.g., fuel) and ignited. Once ignited, the compressed air-combustion product mixture is converted to a hot pressurized exhaust gas (hot gas) that flows through gas turbine component 206. The hot gas flows through gas turbine component 206, and specifically, passes over a plurality of blades 212 (e.g., stages of blades) coupled to shaft 208, which rotates blades 212 and shaft 208 of turbo machine 200. As shaft 208 of turbo machine 200 rotates, compressor 202 and gas turbine component 206 are driven and generator 210 may create power (e.g., electric current).

Shrouds 214 of gas turbine component 206 may prevent axial leakage of the hot gas as it flows through gas turbine component 206. As shown in FIG. 2, shroud 214 may be coupled to housing 216 of gas turbine component 206 and may be positioned adjacent blades 212. In an alternative embodiment, not shown, shroud 214 may be coupled to the tip of each of the blades 212 and may be coupled to one another to form a substantially continuous ring that may rotate with blades 212 for preventing axial leakage of the hot gas within gas turbine component 206. Blades 212 can have holes that are drilled into blades 212, such as for purposes of cooling. Applicants have discovered that holes in blades 212 that are not drilled to proper tolerance and/or drilled by improper process, such as an over drill, are possible source of failure of a blade 212.

Figure 3:
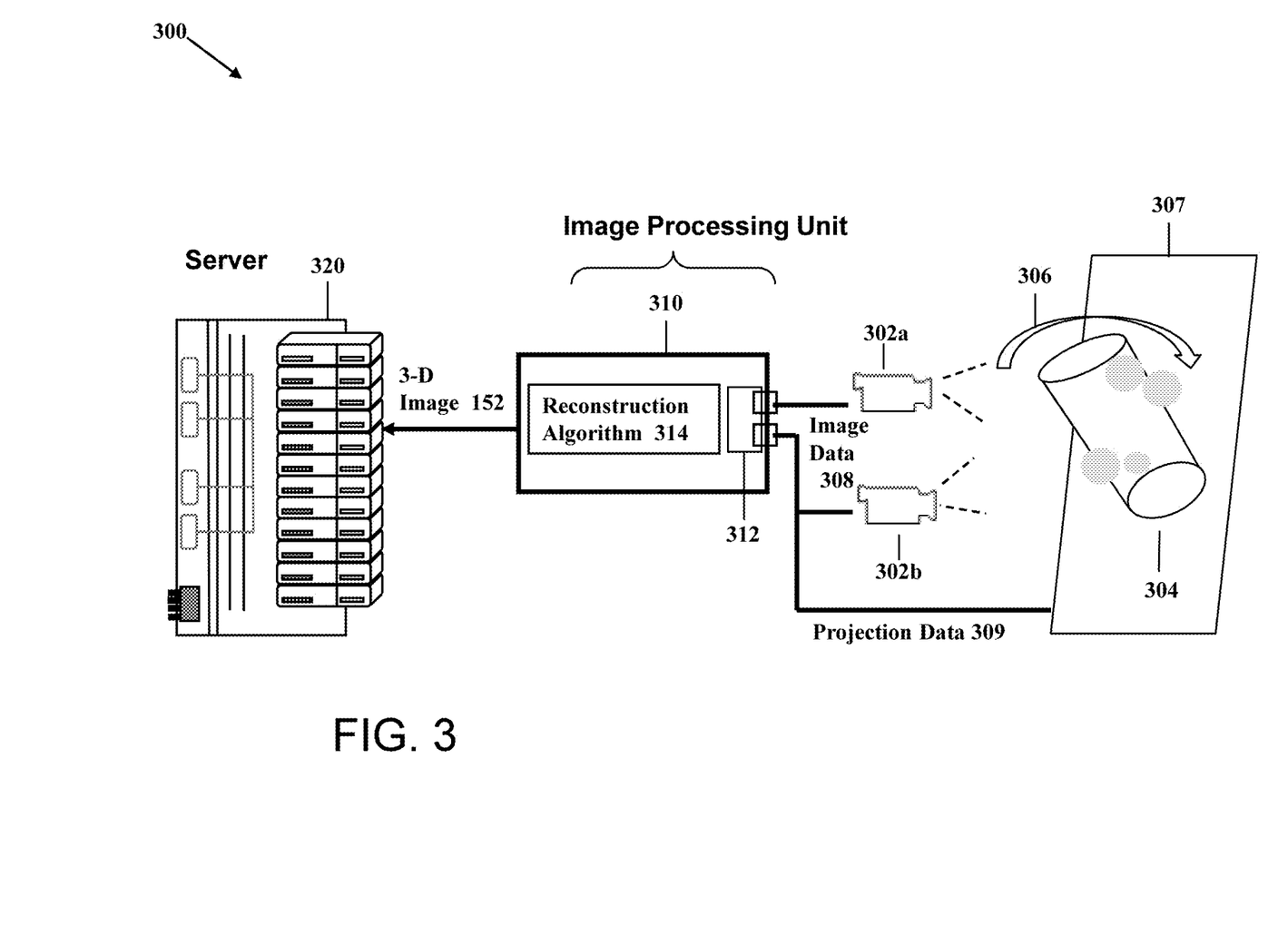
FIG. 3 shows obtaining of a three-dimensional image according to embodiments of the present invention.

Referring now to FIG. 3, a system 300 for obtaining a three-dimensional image according to embodiments of the present invention is shown. System 300 includes one or more imaging devices 302a, 302b. Imaging devices 302a, 302b gather image data 308 and/or projection data 309 from an object 304. To this extent, imaging device 302a, 302b can utilize any technology that is now known or later developed for gathering both surface and internal image data 308 and/or projection data 309 about an object 304, including, but not limited to X-ray, magnetic resonance imaging (MRI), computed tomography (CT), and/or the like. In the case that CT is utilized, one or more of imaging devices 302a, 302b can utilize an x-ray source, a linear array of detectors, and/or a two dimensional digital detector. As x-rays from imaging device 302a, 302b pass through object 304, some of the x-rays are absorbed by the material in the object 304 while others pass completely through the object and fall on a detector 307 positioned opposite the object 304 from imaging devices 302a, 302b. This detector 307 collects these signals that have passed through the object 304, as projection data 309. This projection data 309 can be forwarded to a reconstruction unit 310 to be reconstructed using a reconstruction algorithm 314 that can generate a 2 dimensional or three dimensional image of the part that is being imaged. Object 304 can be rotated and/or translated 306 and the image data 308 and/or projection data 309 collected therefrom can also be forwarded to reconstruction unit 310 for processing. Reconstruction unit 310 combines image data 308 and/or projection data 309 to generate 3D image 152, which can be sent to a server 320 or other computer device, such as a computer device included in computer system 102, for storage and/or further processing.

Applicants have discovered that challenges exist in evaluating 3D images 152, such as those obtained using system 300 as described above. Even though these technologies provide non-destructive evaluation, which can detect density variations as small as 2% in material, the data provided using these techniques is often very voluminous. As such, evaluating such a large amount of image data 308 that is found in such a 3D image 152 can absorb significant time and/or resources. This can be further exacerbated for objects that have a complex shape, such as a gas turbine blade, for example.

Referring again to FIG. 1, planar surface generator module 144, as executed by computer system 102, generates a planar surface that is based on a surface or "peel" of the 3D image 152, which may not be planar. Peel, when used in this context, refers to a thin section of 3D image 152 that is not necessarily planar, sometimes following a contour of 3D image 152. To this extent, peel can be located at the external surface of 3D image 152, an internal surface of the 3D image 152 or, in the alternative, can be any of many underlying layers 3D image 152 that follow the contours of the external surface, internal surface, or other surface of 3D image 152. To this extent, the surface that is generated in the present invention can be generated by interpolating points located on the peel. One commonly used structure for interpolating such points is referred to as non-uniform rational B-Spline (NURBS). In any case, once such a surface is generated, planar surface generator module 144 can utilize a curved reformat function to generate the planar surface from the peel surface. A curved reformat function visualizes data on any curved surface (in 3D) and converts it into a planar two-dimensional (2D) image. A first slice can be specified in the XZ plane of 3D image 152 and points can be selected on the XY plane of 3D image 152 to define a curve. In order to accomplish this, 3D image 152 can be provided to a user, such as via a graphical user interface, and points used to perform an interpolation could be defined in either a 2D-view or in a 3D view.

Figure 4A:
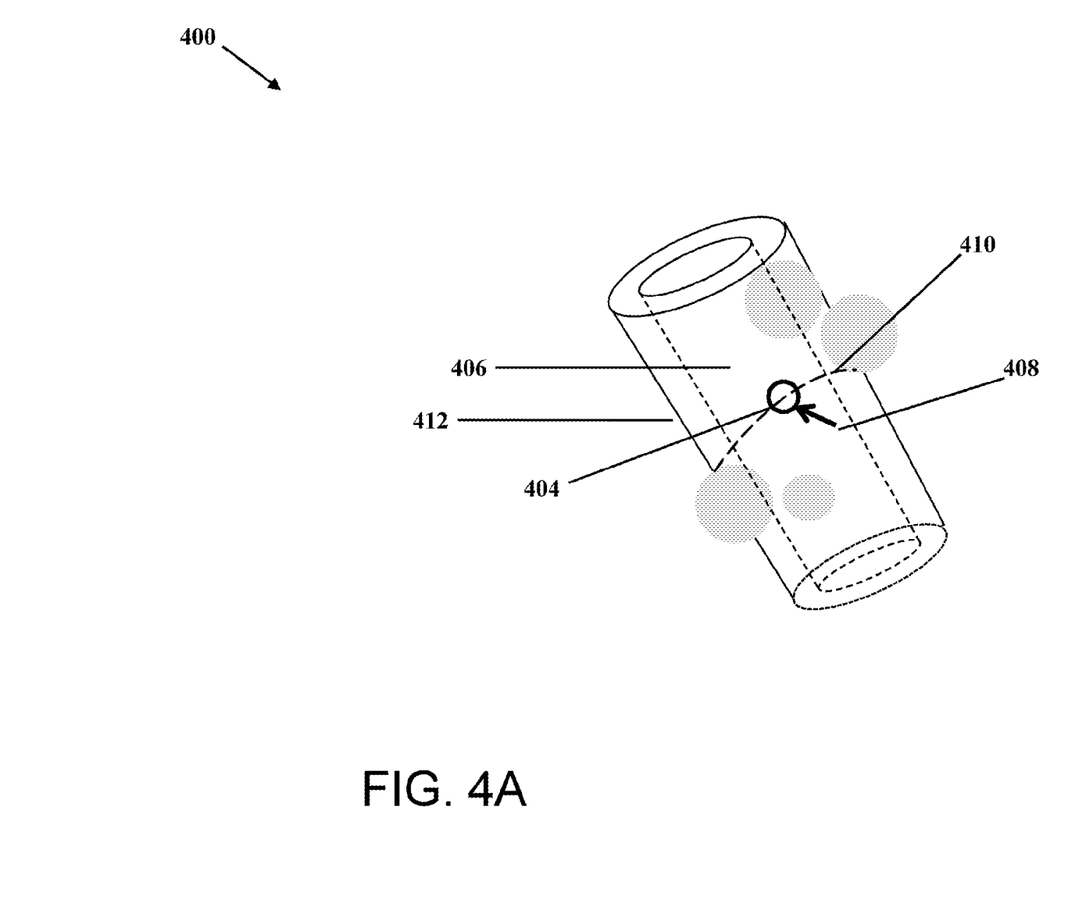
FIG. 4A-C show a set of orthographic views of an image according to embodiments of the present invention.
Figure 4B:
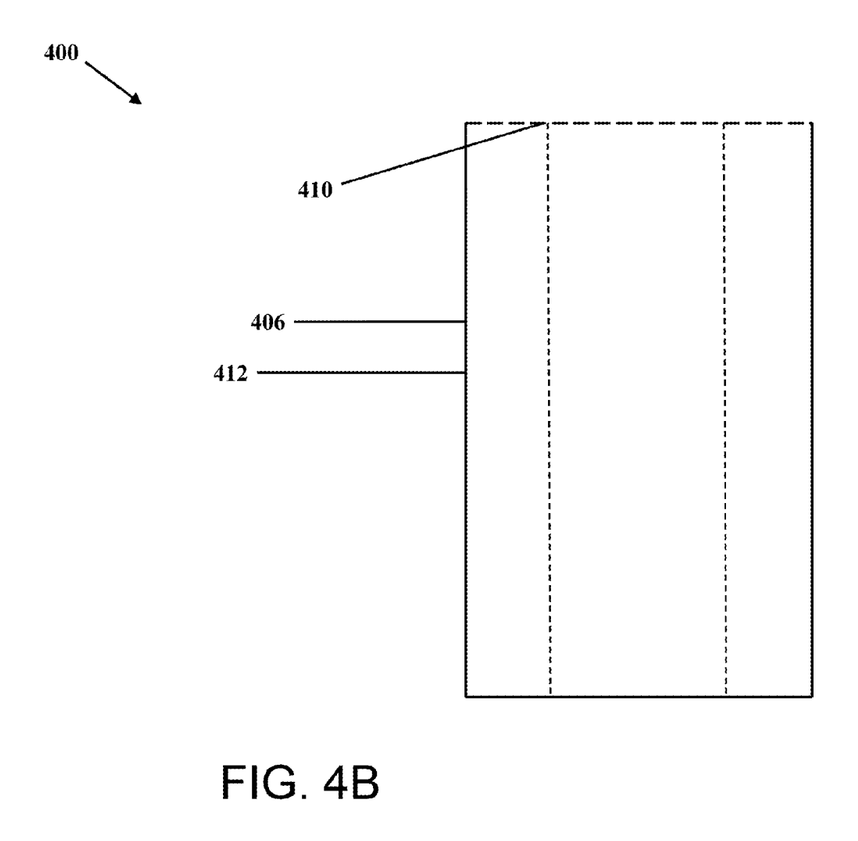
Figure 4C:
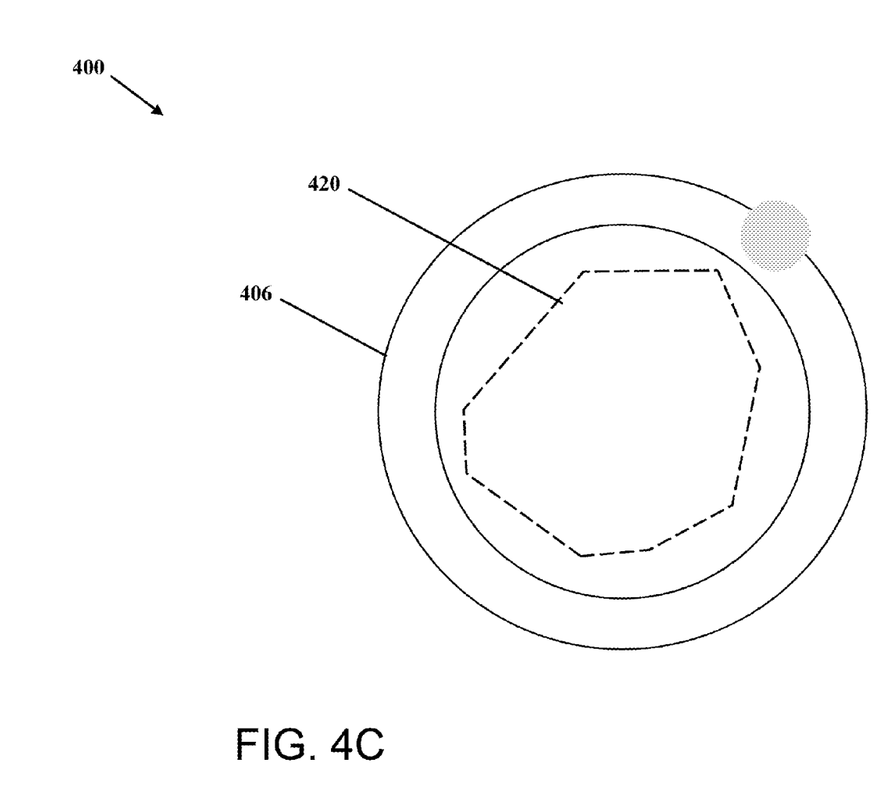

Turning now to FIG. 4A-C, a set of orthographic views 400 of a 3D image 152 (FIG. 1) according to embodiments of the present invention is shown. FIG. 4A shows a view 400 of 3D image 152 (FIG. 1) in an XYZ 3D orientation. FIG. 4B shows view 400 of 3D image 152 (FIG. 1) in a YZ orientation. FIG. 4C shows view 400 of 3D, image 152 (FIG. 1) in a XZ orientation. One or more of these views can be provided to a user 120 using a graphical user interface (GUI) or using any other solution. A user 120 can select one or more points 404 on a surface 406 of view 400, such as with a selection device 408. Based on the location of points 404, a surface 420 (e.g., a NURBS surface) can be interpolated. Surface 420 can be interpolated from point 404 (e.g., as part of a set of points) in using any solution now known or later developed.

In one embodiment, point 404 can be used to define a spline 410, which can then be used to interpolate the surface 420. In a mathematical sense, spline 410 is a sufficiently smooth polynomial function that is piecewise defined, and possesses a high degree of smoothness at the places where the polynomial pieces connect. This spline 410, once defined, can be used as a factor in a curved reformat function to convert a curved surface 406 into a planar surface having the characteristics of the curved surface 406. As applied to the invention, spline 410 can be defined by using point 404 in conjunction with another point (not shown) selected by user 120 (FIG. 1). Alternatively, point 404 can be used in conjunction with a default axis (not shown) of view 402 to generate spline 410. Alternatively, an edge 412 of view 402 can be used to generate spline 410. For example, if point 404 is located on edge 412, the contour of edge 412 can be used for spline 410. Further, if point 404 is not located on edge 412, point 404 can be snapped to the nearest edge 412 and that can be used as the spline. Once spline 410 has been defined, one or more additional splines (not shown) can be formed in a similar manner to those described above.

Figure 5:
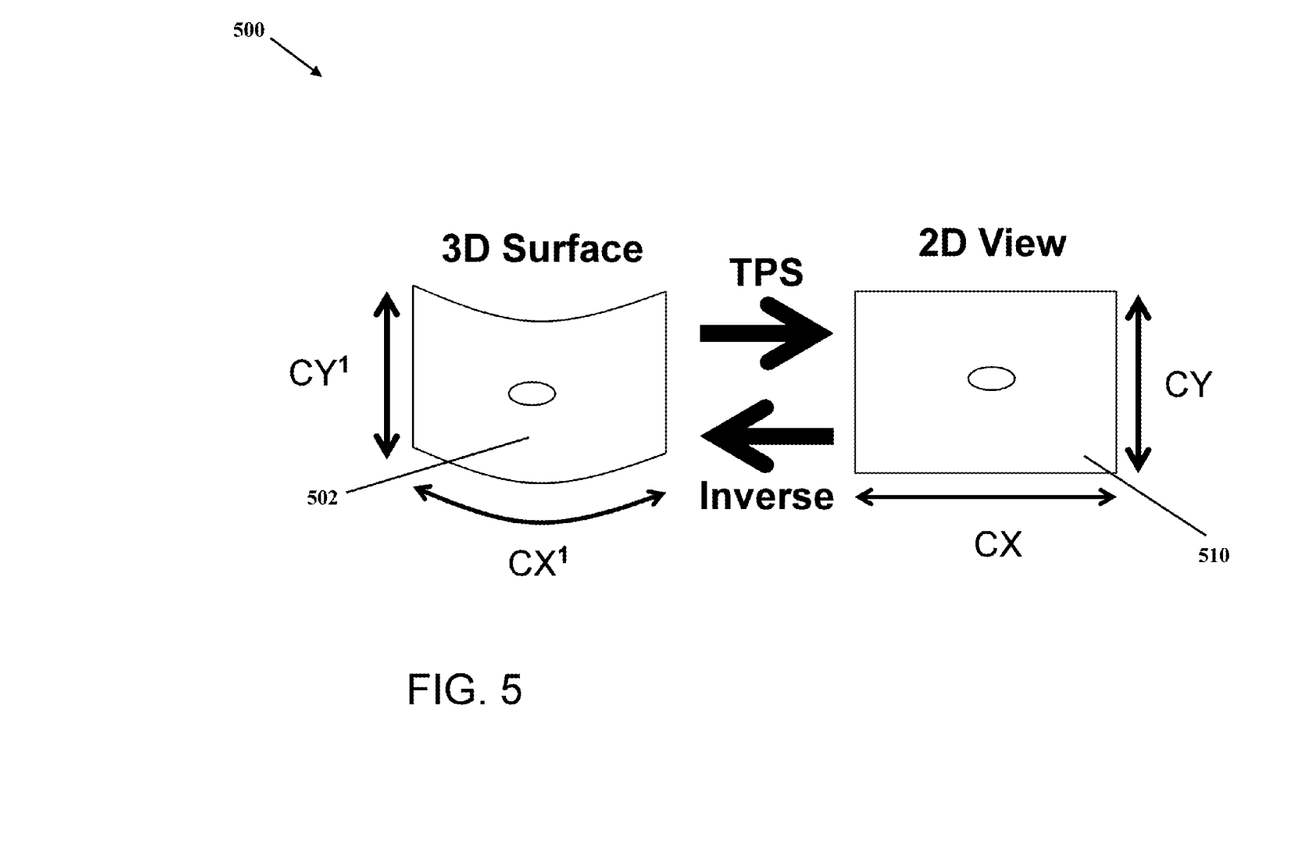
FIG. 5 shows a schematic diagram illustrating generating a planar surface according to embodiments of the present invention.

Referring now to FIG. 5, in conjunction with FIG. 4, generating of a planar surface 502 is shown. In an embodiment in which a spline is defined, the defined spline 410 can be joined to the second spline and/or any number of subsequently defined splines thru interpolation techniques to form a surface 502. The surface can be generated through interpolating between the points 404 and/or the splines 410. One commonly used method to describe such a surface are NURBS. The intersection of this surface 420 and the 3D image 152 (FIG. 1) can be obtained, and the pixel values of this intersection can be converted into a planar 2D image 510 using curved reformat function. Curved reformat function is accomplished using transformations, including but not limited to thin spline, bilinear transformation and/or affine transform, or the like, for converting the curved surface 407 of 3D image 152 (FIG. 1) to a planar 2D image 510. In the alternative, these transformations can be performed concurrently with the joining of the splines 410 to obtain the planar 2D image 510. As stated above, planar 2D image 510 can be coincident with the external geometry of the object, can be coincident with an internal geometric surface, or can be at any location within 3D image 152 (FIG. 1).

Figure 6:
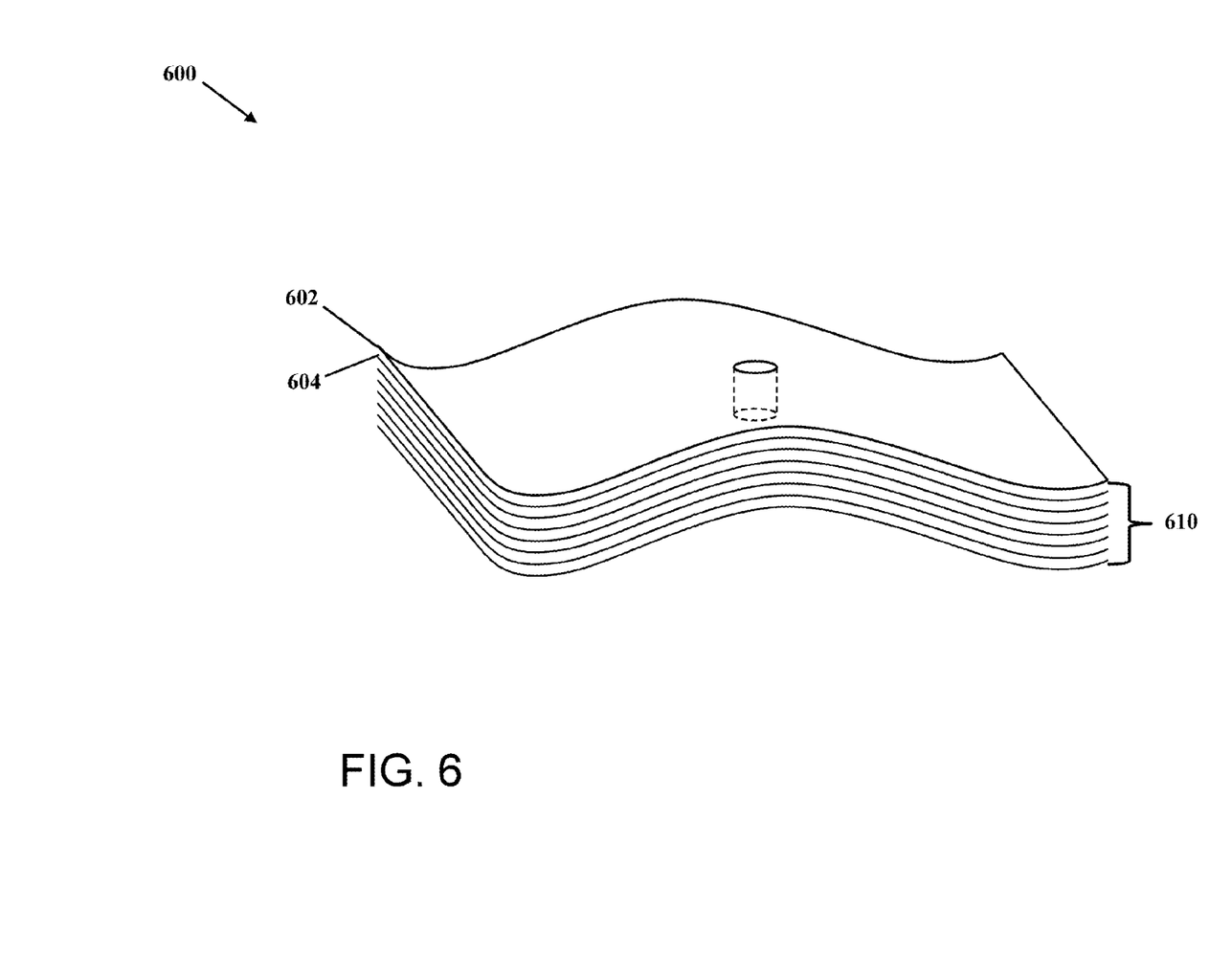
FIG. 6 shows a schematic diagram illustrating removing a peel from the three-dimensional image according to embodiments of the invention.

Referring again to FIG. 1, adjacent peel retrieval module 146, as executed by computer system 102, retrieves a peel that is adjacent to the surface 406 of 3D image 152 from which the planar 2D image was created. Referring now to FIG. 6, retrieval of a peel 604 from a 3D image 600 according to embodiments of the invention is shown. Surface 602 represents the surface 406 (FIG. 4) of 3D image 600 to which the curved reformat function has been applied and, thus, for which planar 2D image 510 (FIG. 5) has been generated. Although shown as an exterior surface, any of layers 610 can form the initial surface. To this extent, peel 604 represents the portion of 3D image 600 that is directly adjacent to and that runs parallel with surface 602. To this extent, peel 604 could be located directly interior to surface 602 of 3D image 600 or, in the alternative could be directly exterior to surface 602. In case of an interior peel 604, the peel 604 could be slightly enlarged to correspond in size to the adjacent surface. Alternatively, in case of an exterior peel 604, the peel could be slightly reduced to correspond in size to the adjacent surface.

Referring again to FIG. 1, planar surface generator module 144, as executed by computer system 102, generates a second planar surface that is based on the peel 604 of 3D image 152 that was retrieved by adjacent peel retrieval module 146, which may not be planar and/or is derived in one of the ways described for the first surface. This generating can be performed using a curved reformat function, similar to the curved reformat, described above, used to generate the planar surface from the original surface 602 of the 3D image 152. The curved reformat function can be generated using the same points from the original generating. For example, the individual points from the previously evaluated surface 602 can be translated to the peel 604. Any individual point could have a separately defined translation path, or, in the alternative, a single translation path could be used to translate multiple or all points. Each translation path could be defined in one or more of the following: (1) manually by the user, (2) using the normal of the surface at the respective point, and/or (3) using any other computation for that point based on the 3D image 152 including but not limited to computing the direction of fibers in the material that comprises the object from which 3D image 152 was obtained. Based on the translated points, a new surface can be generated.

This translation of points would result in a second planar surface that has an orientation that approximately corresponds to the orientation of the original planar surface. This corresponding alignment of surface resulting from the translated data points can result in analysis that requires fewer resources than would be required if a complex transformation were performed and the resulting surfaces required alignment with respect to one another prior to analysis. It should be understood that the invention is not limited to two planar surfaces. Rather, peels can be retrieved, and the resulting peels can also have planar surfaces generated therefrom, using the curved reformat function. Furthermore, additional intermediate peels can be created in between two surfaces using interpolation between them. As can be appreciated, a stacking of the resulting similarly aligned planar surfaces can allow for more cost effective analysis. The stacked 2D planar surfaces can, themselves, be viewed as a 3D image, which, for example, could be rendered or further analyzed. To this extent, the invention could result in a transformation of the original 3D image into a new 3D image that requires fewer resources to analyze.

Referring again to FIG. 1, planar surface analyzer module 148, as executed by computer system 102, analyzes the 2D planar surface, the second 2D planar surface, and/or any other generated 2D planar surfaces to determine characteristics of the object from which the 3D image was obtained. To accomplish this, planar surface analyzer module 148 could look at any gradient differences between the regions in the reformatted 2D planar surface and could identify any significant features, including, but not limited to drillings, morphology of the surface, inclusions, fibers, and/or the like and/or defects such as delamination, debonds, porosity cracks etc. As can be appreciated, a stacking of the planar surfaces having the same alignment, resulting from the curved reformat and the peeling can produce a stack of planar surfaces that accurately depict the three-dimensional characteristics of the 3D image 152.

Figure 7:
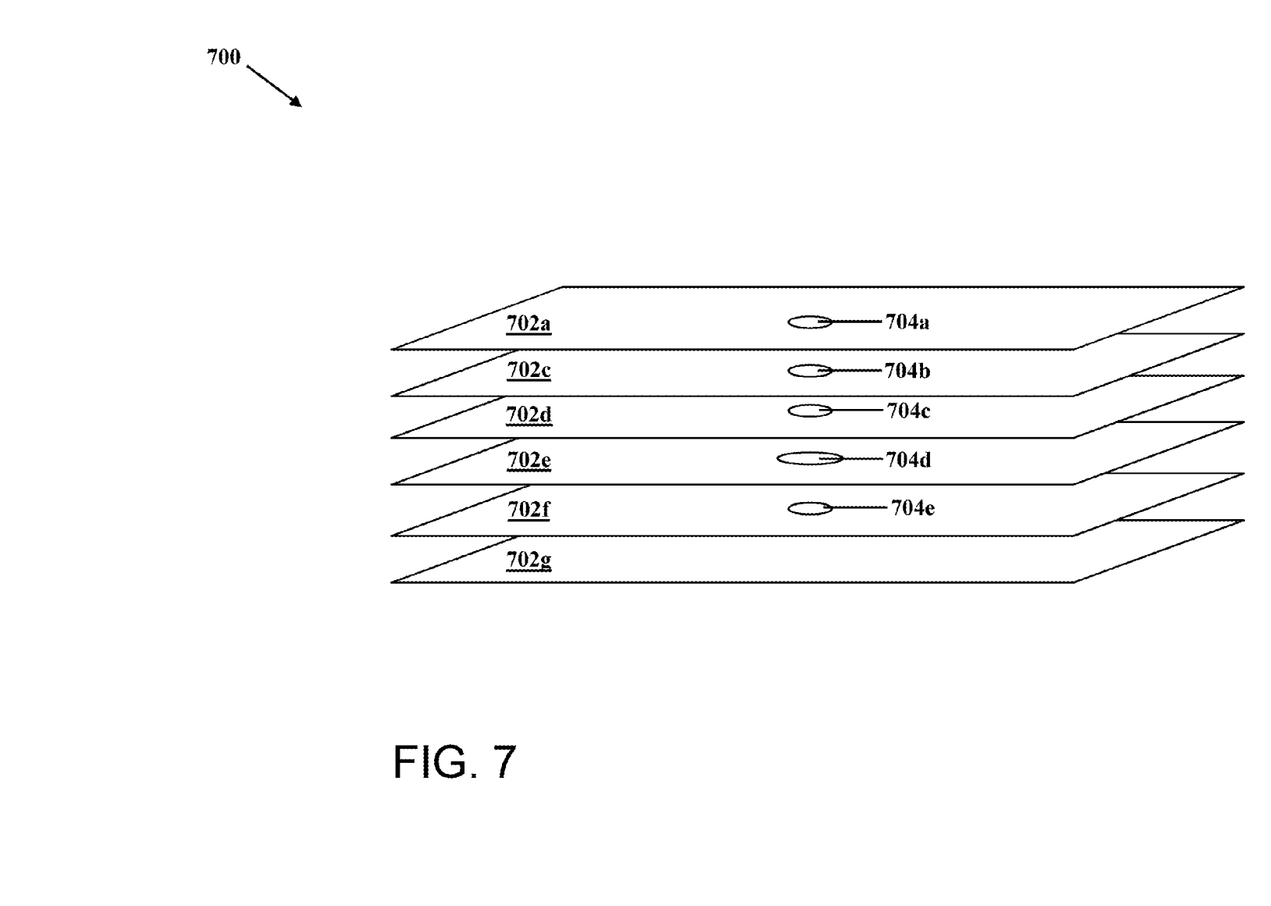
FIG. 7 shows an illustrative group of planar surfaces according to embodiments of the invention.

Referring now to FIG. 7, an illustrative analysis group 700 having a plurality of planar surfaces 702*a-g* is shown. As shown, analysis group 700 has at least two planar surfaces 702*a-g* grouped in order, with planar surface 702*a* being the initial and planar surface 702*g* being the ultimate planar surface of the analysis group 700. Each of the planar surfaces 702*a-g* is the result of a curved reformat function having been performed on either an original surface 406 (FIG. 4) or an adjacent peel that was retrieved based on the location of the previous surface/peel. It should be understood that even though the shapes of planar surfaces 702*a-g* are shown as been roughly quadrilateral in the XY axis, any other shape is envisioned. In any case, as shown, a hole in the original 3D object is reflected in a series of 2D circular apertures 704*a-f* in planar surfaces 702*a-f*. Planar surface analyzer module 148 (FIG. 1) could analyze analysis group 700 to determine whether tolerances have been met. For example, a determination could be made that the hole was too deep, and that the hole was supposed to extend only to planar surface 704*d*, rather than planar surface 704*e*. Further, such an analysis would also be able to determine certain anomalies, e.g., that the portion of the hole 704*d* through planar surface 702*d* has a larger diameter than desired. Still further, the visualization of the reformatted 3D image accomplished by the stacking of 2D planar surfaces can reduce the difficulty of inspecting of the object.

Figure 8:
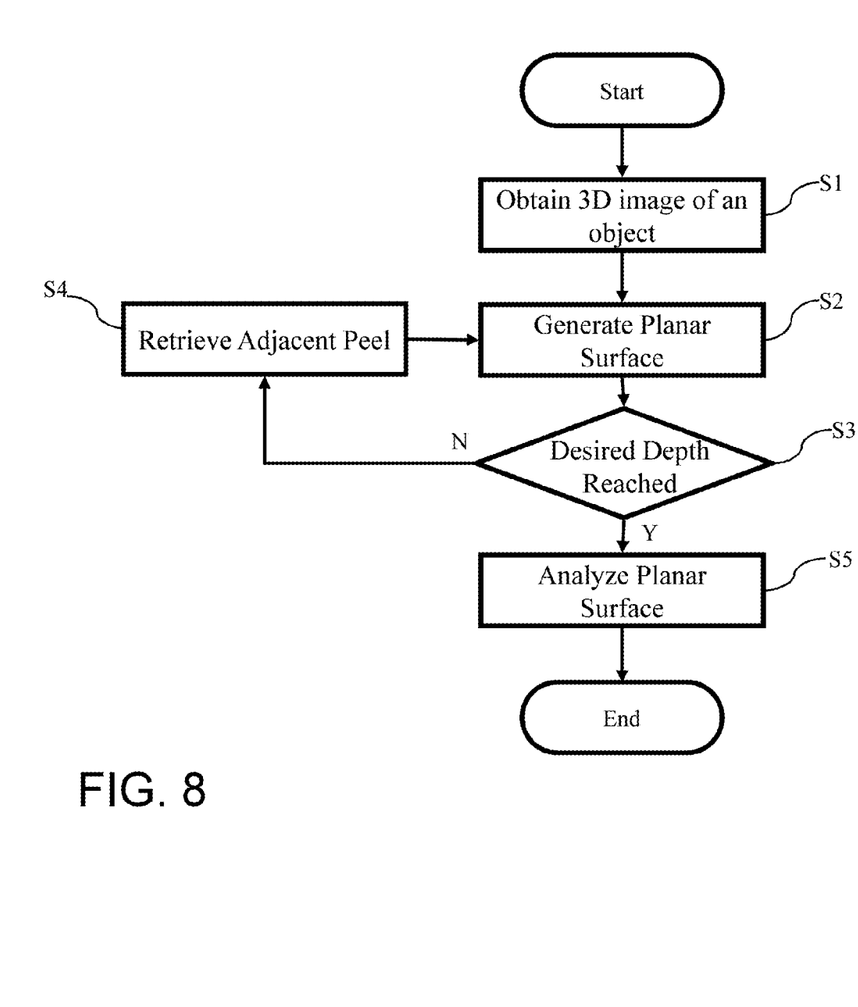
FIG. 8 shows an example flow diagram according to embodiments of the invention.

Turning now to FIG. 8, an example flow diagram according to embodiments of the invention is shown. As illustrated in FIG. 6 in conjunction with FIG. 1, in S1, 3D image obtainer module 142, as executed by computer system 102, collects a 3D image 152 of an object. This 3D image can be collected with an imaging device 302a-b (FIG. 3), using a technology such as a MRI, CT or the like. In S2, planar surface generating module 144, as executed by computer system 102, generates a planar surface with a curved reformat function using a surface of the 3D image 152. In S3, a determination is made as to whether the desired depth within the 3D image 152 has been reached for generating planar surfaces. If not, in S4, adjacent peel retrieval module 146, as executed by computer system 102, retrieves a peel of the 3D image 152 that is adjacent to the previously evaluated surface/peel. This peel can be used to generate another planar surface in S2. If the determination in S3 is that the desired depth has been reached, flow moves to S5, planar surface analyzing module 148, as executed by computer system 102, analyzes the planar surfaces to determine a characteristic of the object.

While shown and described herein as a method and system for analyzing a 3D object, it is understood that aspects of the invention further provide various alternative embodiments. For example, in one embodiment, the invention provides a computer program fixed in at least one computer-readable medium, which when executed, enables a computer system to analyze a 3D object. To this extent, the computer-readable medium includes program code, such as 3D object analyzer program 140 (FIG. 1), which implements some or all of a process described herein. It is understood that the term "computer-readable medium" comprises one or more of any type of tangible medium of expression, now known or later developed, from which a copy of the program code can be perceived, reproduced, communicated, or otherwise executed by a computing device. For example, the computer-readable medium can comprise: one or more portable storage articles of manufacture; one or more memory/storage components of a computing device; and/or the like.

In another embodiment, the invention provides a method of providing a copy of program code, such as 3D object analyzer program 140 (FIG. 1), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for analyzing a 3D object. In this case, a computer system, such as computer system 120 (FIG. 1), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; and/or the like.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," if/when used in this specification, specify the presence of stated features, integers, steps, operations, elements, and/or components, but do not preclude the presence or addition of one or more other features, integers, steps, operations, elements, components, and/or groups thereof.

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for analyzing an object, the method comprising:
    generating, using a computer device, a planar surface from a curved reformat function based on a surface of a 3D image of an object;
    determining, using the computer device, a peel of the 3D image, the peel being an adjacent surface of the 3D image that is parallel to the surface of the 3D image; and
    generating using the computer device, a second planar surface from a curved reformat function based on the peel; and
    analyzing using the computer device, the planar surface and the second planar surface to determine a characteristic of the object.

2. The method of claim 1, further comprising: gathering a set of image data from the object using an imaging device.

3. The method of claim 1, the generating further comprising:
    selecting at least one first point located on a first plane within the 3D image;
    defining a first spline based on the at least one first point;
    selecting at least one second point located on a second plane within the 3D image;
    defining a second spline based on the at least one second point; and
    generating the surface based on the first and second splines.

4. The method of claim 3, wherein the set of points are selected by a user via a graphical user interface (GUI).

5. The method of claim 3, wherein the spline is generated based on the at least one first point and at least one of:
    an additional point, selected by a user, on the first plane on the 3D image;
    an edge calculated to be nearest the at least one first point; or an edge contour containing the at least one first point.

6. The method of claim 1, further comprising: translating the surface of the 3D image within the 3D image.

7. The method of claim 1, further comprising: scaling the surface of the 3D image with respect to a normal to the surface of the 3D image.

8. The method of claim 1, wherein the 3D object is a part of a turbine blade.

9. The method of claim 1, wherein the characteristic includes the depth of a hole.

10. A system for analyzing an object comprising at least one computer device that performs a method, comprising:
   generating a planar surface from a curved reformat function based on a surface of a 3D image of an object;
   determining a peel of the 3D image, the peel being an adjacent surface of the 3D image that is parallel to the surface of the 3D image;
   generating a second planar surface from a curved reformat function based on the peel; and
   analyzing the planar surface and the second planar surface to determine a characteristic of the object.

11. The system of claim 10, the method further comprising:
   gathering a set of image data from the object using an imaging device.

12. The system of claim 10, the generating further comprising:
   selecting at least one first point located on a first plane within the 3D image;
   defining a first spline based on the at least one first point;
   selecting at least one second point located on a second plane within the 3D image;
   defining a second spline based on the at least one second point; and
   generating the surface based on the first and second splines.

13. The system of claim 12, wherein the point is selected by a user via a graphical user interface (GUI).

14. The system of claim 12, wherein the spline is generated based on the point and at least one of:
   an additional point, selected by a user, on the first plane on the 3D image;
   an edge calculated to be nearest the at least one first point; or an edge contour containing the at least one first point.

15. The system of claim 10, wherein the 3D object is a turbine blade.

16. The system of claim 10, wherein the characteristic includes the depth of a hole.

17. A program product stored on a non-transitory, computer readable storage device with instructions encoded thereon for analyzing an object, which, when executed, performs a method, comprising:
   generating a planar surface from a curved reformat function based on a surface of a 3D image of an object;
   determining a peel of the 3D image, the peel being an adjacent surface of the 3D image that is parallel to the surface; and
   generating a second planar surface from a curved reformat function based on a remainder surface of the remainder 3D image; and
   analyzing the planar surface and the second planar surface to determine a characteristic of the object.

18. The program product of claim 17, the generating further comprising:
   selecting at least one first point located on a first plane within the 3D image;
   defining a first spline based on the at least one first point;
   selecting at least one second point located on a second plane within the 3D image;
   defining a second spline based on the at least one second point; and
   generating the surface based on the first and second splines.

19. The program product of claim 18, wherein the spline is generated based on the point and at least one of:
   an additional point, selected by a user, on the first plane on the 3D image;
   an edge calculated to be nearest the at least one first point; or an edge contour containing the at least one first point.

20. The program product of claim 17, wherein the 3D object is a part of a turbine and wherein the characteristic includes whether an over drill has occurred.

* * * * *